(12) United States Patent
Lindberg et al.

(10) Patent No.: US 6,611,320 B1
(45) Date of Patent: Aug. 26, 2003

(54) METHOD AND APPARATUS

(75) Inventors: Lars-Göran Lindberg, Linköping (SE); Gunnar Enlund, Norrköping (SE); Magnus Vegfors, Linköping (SE)

(73) Assignee: OptoQ AB, Linkoping (SE)

( * ) Notice: Subject to any disclaimer, the term of this patent is extended or adjusted under 35 U.S.C. 154(b) by 166 days.

(21) Appl. No.: 09/657,305

(22) Filed: Sep. 7, 2000

Related U.S. Application Data

(60) Provisional application No. 60/203,077, filed on May 9, 2000, and provisional application No. 60/152,614, filed on Sep. 8, 1999.

(51) Int. Cl.$^7$ .......................... G01N 33/48; G01N 33/72
(52) U.S. Cl. ........................ 356/40; 600/320; 600/328; 436/66
(58) Field of Search ................................. 600/323, 320, 600/322, 328, 368; 356/41, 40, 42; 436/66

(56) References Cited

U.S. PATENT DOCUMENTS

| | | | | |
|---|---|---|---|---|
| 4,925,299 A | * | 5/1990 | Meisberger et al. | 356/40 |
| 5,149,503 A | * | 9/1992 | Kohno et al. | 422/82.05 |
| 5,167,230 A | * | 12/1992 | Chance | 600/323 |
| 5,194,909 A | * | 3/1993 | Tycko | 356/40 |
| 5,203,342 A | * | 4/1993 | Sakai | 600/504 |
| 5,219,400 A | * | 6/1993 | Jacot et al. | 600/320 |
| 5,377,674 A | * | 1/1995 | Kuestner | 600/328 |
| 5,490,523 A | * | 2/1996 | Isaacson et al. | 600/323 |
| 5,706,821 A | * | 1/1998 | Matcher et al. | 600/310 |
| 5,720,284 A | | 2/1998 | Aoyagi et al. | |
| 5,755,226 A | | 5/1998 | Carim et al. | |
| 5,773,301 A | * | 6/1998 | Ziegler | 436/66 |
| 5,851,835 A | * | 12/1998 | Groner | 436/63 |
| 5,898,487 A | * | 4/1999 | Hage | 356/39 |

FOREIGN PATENT DOCUMENTS

| | | |
|---|---|---|
| EP | 0762108 A2 | 3/1997 |
| WO | WO 89/01758 A1 | 9/1989 |
| WO | WO 96/37259 A1 | 11/1996 |
| WO | WO 97 15229 A1 | 5/1997 |

\* cited by examiner

*Primary Examiner*—Richard A. Rosenberger
*Assistant Examiner*—Vincent P Barth
(74) *Attorney, Agent, or Firm*—Birch, Stewart, Kolasch & Birch, LLP

(57) ABSTRACT

The present invention relates to a method for detecting blood characteristics including hemoglobin in a fluid medium using both transmission and reflection of a light beam which forms a quotient.

20 Claims, 13 Drawing Sheets

Experimental set-up.

Fig. 16 The PPG signal during blood dilution in the radial artery.

METHOD AND APPARATUS

This application claims priority under 35 U.S.C. §119(e) based on (Provisional Application No. 60/152,614 filed Sep. 8, 1999, and (2) Provisional application No. 60/203,077 filed May 9, 2000.

The present invention relates to a non-invasive method for determination of blood characteristics including hemoglobin (EVF/haematocrit) in a vessel containing a mixture of liquid and blood cells using the orientation effects of the red blood cells. The present invention also relates to an apparatus for performing the, method.

BACKGROUND TO THE INVENTION

There are different non-invasive methods known for measurement of hemoglobin. These methods make use of absorption of energy at a certain light wavelengih of the red blood cells (RBCs). Carim et al disclose in U.S. Pat. No. 5,755,226 a non-invasive method and apparatus for the dirct non-invasive prediction of hematocrit in mammalian blood using photopletysmography (PPG) techniques and data processing. However, this method only makes use of the ability of the RBCs to absorb energy. This method is also quite complicated regarding the formulas which are to be used when calculating the predicted hematocrit. Thus the method is time consuming. This method has not taken into account the red blood cell orientation and distribution in blood vessels.

Further, a method and an apparatus, are disclosed in WO 97/15229 for determining hemoglobin concentration in blood. The method is used for detecting hemoglobin in the microvascular system beneath the mucosal membranes on the inside of the lip of a human subject by introducing a measuring tip into the mouth of a subject. This means that the measuring tip of the apparatus must have some kind of sterile shell before it may be placed in the mouth. This sterility of the measuring tip means that either the apparatus must be autoclaved before measuring or that a disposable plastic tip has to be used when performing the method. This method further uses the reflection of light for determining the concentration of hemoglobin.

Accordingly, there is a need for new methods for detecting hemoglobin which takes into account the blood cell orientation and thus gives a more accurate detection value. Further, methods which do not involve an extra step of making the apparatus sterile before measuring or disposable tips are desirable. The new methods should also be less sensitive to variations in the blood pressure, e.g. the pulsative, (systolic) pressure.

SUMMARY OF THE INVENTION

In accordance with a first aspect of the present invention there is provided a new non-invasive method for determination of blood characteristics including hemoglobin from a mixture of liquid and blood cells contained in a light pervious vessel comprising:

a) directing at least one light beam against the vessel;
b) detecting the intensity of the light of said light beam transmitted through the vessel;
c) detecting the intensity of the light of said light beam reflected from the vessel;
d) calculating a quotient of said detected intensity of said transmitted light and detected intensity of said reflected light or a quotient of said detected intensity of said reflected light and detected intensity of said transmitted light; and
e) analyzing said quotient to determine the blood characteristics.

In accordance with a second aspect of the present invention there is provided an apparatus for determination of blood characteristics including hemoglobin from a mixture of liquid and blood cells contained in a light pervious vessel comprising:

i) at least one light source for directing a light beam against the vessel;
ii) a first detector for detecting the intensity of the light of said light beam transmitted through the vessel;
iii) a second detector for detecting the intensity of the light of said light beam reflected from the vessel; and
iv) a processor for calculating a quotient of said intensity of said transmitted light detected by said first detector and said intensity of said reflected light detected by said second detector or a quotient of said intensity of said reflected light detected by said second detector and said intensity of said transmitted light detected by said first detector, and for analyzing said quotient to determine the blood characteristics including hemoglobin; and optionally
v) registration means for storing the blood characteristics; and optionally
vi) means for visualization for visualizing the blood characteristics.

Preferably the processor is adapted to convert the quotient to a concentration value of the determined blood characteristics. This adaption may be performed by using a calibration curve.

In accordance with a third aspect of the present invention there is provided use of an apparatus according to the second aspect of the present invention in a dialysis apparatus (or dialysis device).

DETAILED DESCRIPTION OF THE INVENTION

With the expression "blood characteristics" is meant in the present application characteristics of blood such as concentration of blood components, e.g. hemoglobin, total hemoglobin, red blood cells, white blood cells, platelets, cholesterol, albumin, thrombocytes, lymphocytes, drugs and other substances, viscosity, blood pressure, blood flow, blood volume, blood cell illnesses, abnormal blood cell appearances, anaemia, leukemia, lymphoma.

With the expression "hemoglobin" is meant in the. present application oxyhemoglobin, reduced hemoglobin, carboxy hemoglobin, methemoglobin and sulphhemoglobin.

With the expression "red blood cells", also known as erythrocytes, is meant in the present application whole or partly lysed red blood cells which contain hemoglobin.

With the expression "light pervious vessels" is meant in the present application a blood vessel in an animal, a pipe, a tube or a tubing which is light pervious. The pipe, tube or tubing may be manufactured from acrylonittile butadiene styrene (ABS), polycarbonate or acrylic glass (polymethylmethacrylate; PMMA) which gives a non-flexible material or from polyvinyl chloride (PVC) or silicon rubber, plasticized PVC, e.g. PVC plasticized with dioctylphtalate, diethylhexylphtalate or trioctyltrimellitate, which gives a flexible material. PMMA is the most preferred non-flexible material. The light pervious vessel may be used when performing liquid transfusions or blood transfusions. The elasticity of the material may be varied in a wide range. The animal containing a blood vessel is preferably a mammal, most preferred a human being.

As used herein, "light" refers generally to electromagnetic radiation at any wavelength, which includes the infrared, visible and ultraviolet portions of the spectrum. A particularly preferred-portion of the spectrum is that portion where there is relative transparency of the tissue, such as in the visible and near-infrared wavelengths. It is to be understood that for the present invention, light may be nonpolarized or polarized light, coherent light or incoherent light and illumination may be steady pulses of light, amplitude modulated light or continues light.

Light sources which may be used in the method and the apparatus according to the invention are e.g. light emitting diodes (LEDs), laser diodes or combinations thereof such as VCSEL (vertical cavity surface emitting laser). Preferably less expensive LEDs are used. Today there are also new strong light emitting diodes which may be used in the method and the apparatus according to the invention. Flash lamp light sources are also conceivable for use in the present invention. The light source may further be capable of emitting monochromatic light, i.e. a monochromator. Optical fibres for guiding the light to and from the measured spot and/or quartz halogen lamps or tungsten lamps may also be used as light sources. Optical light fibres and or direct illumination on the measured spot may also be used.

Detectors which may be suitable for use when performing the method according to the present invention, are phototransistors, photodiodes, photomultipliers, photocells, photodetectors, optical power meters, amplifiers, CCD arrays and so on.

According to one preferred embodiment of the method of the present invention, the detected intensity of the light of said light beam transmitted through the vessel, the detected intensity of the light of said light beam reflected from the vessel and/or the quotient of said detected intensity of said transmitted light and detected intensity of said reflected light or a quotient of said detected intensity of said reflected light and detected intensity of said transmitted light, is transmitted over a wireless connection to a unit for performing step e) i.e. analysing said quotient to determine the blood characteristics, preferably using a module for wireless communication. The wireless communication is preferably performed using a Bluetooth™ standard. based communication path.

The method according to the present application is using a wavelength which is from 200 nm to 2000 nm, preferably 770 nm to 950 nm, most preferred approximately 770, 800, 850, 940 or 950 nm. 800 nm is preferred due to independence of oxygen saturation.

The mixture of liquid and blood cells in the method of the present application is preferably flowing, but it may as well be standing such as is the case for a fluid medium in a blood bag. The mixture of liquid and blood cells may comprise plasma or any other liquid as e.g. water or dialysis liquids. The plasma is preferably in or from a mammal. The liquid may as well be any other fluid comprising blood cells which may be obtained during or after the processing of blood.

The method according to the present application gives the advantage that the determination of blood characteristics is independent of blood flow velocity and accordingly independent of blood pressure. This is due to the quotient formed of the reflected and the transmitted light intensities.

Further, the method according to the present application is also characterized by that it may be performed on a mammal such as domestic animals or human beings, preferably on a human being.

The method according to the invention may be performed on any part of the human body or the body as a whole comprising a greater blood vessel, preferably a vein, an arteriole, an artery, most preferred blood vessel with a diameter >0.1 mm. The detection is, according to a preferred embodiment of the present invention, performed on a wrist, a toe or a finger. The detection is preferably performed on a finger on the third phalanx.

The method according to the present invention may, according to a preferred embodiment, be used for determination of blood characteristics including hemoglobin in extracorporeal equipments including e.g. dialysis apparatuses (dialysers), cell savers, dialysis monitors, or on a blood bag device (which includes assemblies), or on a slaughter house device, or on a blood fractionation device. The light pervious vessel, preferably a tube or pipe, may in this embodiment of the present invention have a diameter >0.1 mm. In dialysis apparatuses it may be desirable to see how much hemoglobin which is present in a fluid which is subjected to any form of dialysis, preferably hemodialysis. During dialysis it may be desirable to measure the hemoglobin concentration in order to follow changes in blood volume of the patient. Regarding blood bag constructions and assemblies, the method according to the invention may be applied to tubings, bags, filters or any other component that may be used in association with blood bags which may contain whole blood or buffy coat i.e. concentrate of white blood cells (leukocytes). The method may also be used during blood transfusions on tubings, or during blood donations as well. In slaughter houses, the method according to the present application may be useful when recovering blood from slaughter animals and when further processing that blood to give whole blood for use directly in food or fractionate it to obtain the blood components albumin, immunoglobulins and so on. The method according to the present application may also be used when counting blood cells i.e. a process when you count red and white blood cells. This may be done in an apparatus such as a blood cell counter e.g. a Coulter counter manufactured by oulter Diagnostics of Miami, Fla. The method according to the invention may also be used in association with blood analysing, blood typing or blood gas analysing. The method according to the invention may also be used when fractionating human blood in a blood fractionating unit. It may be desirable to use the method according to the present application when Plasma is obtained from donors. The method may also be useful when obtaining buffy coats from a donor or when these buffy coats are further processed for producing e.g. cytokines such as interferon alpha. The method may be useful to determine how the lysis of the RBC:s are performing during the purification of white blood cells which subsequently after one or more steps involving RBC lysis with e.g. ammonium chloride, are exposed to virus e.g. Sendai virus during incubation in a suitable medium e.g. Eagles Minimal Essential Medium, EMEM.

The method, according to the present application, is preferably performed on a blood vessel, tube or pipe.

According to a preferred embodiment of the present invention the light beam is directed essentially perpendicular to a measuring area of the vessel at a wavelength where a minimal absorbance occurs on the red blood cells.

According to a preferred embodiment of the present invention, at least two light beams are directed against the vessel from two light sources, which are positioned and thus appearing on two different opposite sides of the vessel, and detection of the intensity of the reflected light from and transmitted light through the vessel is performed by at least two detectors, preferably by only two detectors. The light beams are preferably directed from opposite sides of the vessel.

According to yet another preferred embodiment of the method according to the present invention, two light beams are directed against the vessel, from two light sources, (which may be incorporated in the same shell, e.g. a chip), which are positioned and thus appearing on one common side of the measuring object. These light sources may when used together in a chip be lightened alternately. One of the light beams may have a wavelength of from 770 nm to 950 nm and the other may have a wavelength of from 480 nm to 590 nm.

There is also according to the present invention provided an apparatus for performing the method according to the present application. There is also according to the present invention provided an apparatus with at least one light source where the wavelength of the light is from 200 nm to 2000 nm, preferably from 770 nm to 950 nm, most preferred approximately 770, 800, 850, 940 or 950 nm. 800 nm is in the NIR-range.

According to one preferred embodiment of the present invention there is provided an apparatus wherein at least one of the components ii), iii), iv) or v) communicates with each other over a wireless connection, preferably over a module for wireless communication. The module for wireless communication comprises at least one transmitter and one receiver. The apparatus may have one module for wireless communication between the said first three components, i.e. i) light source, ii) first detector and iii) second detector, and iv) the processor and/or one module for wireless communication between iv) the processor and v) the registration means. Preferably the wireless communication is performed using a Bluetooth™ standard based communication path.

By combining the method and the apparatus of the present invention with cable-free communication this allow for broadening the use of said method and apparatus by making it more user-friendly. The cable free communication may allow for internet-billing, patient information follow up and statistics, software package updates and service. The user may by ordering via a modem get the necessary codes to perform a certain number of tests much in the same way as with cellular phones.

The radio communication standard Bluetooth™ has opened the opportunity for cable-free equipment in the hospital environment. Bluetoothm™ technology enables electronic devices to communicate with one another without cables. Bluetooth™ modules comprising a transmitter and a receiver may replace cables in many applications. FIG. 17 shows a system including a computer and a blood characteristics-detector where there is no need for cables between them when using the Bluetooth™ technology.

Bluetooth™ technology, developed by L M Ericsson, may use the ISM band 2.45 Ghz and may ensure interruption-free communication. The system may work with quick frequency hopping of 1,600 hops per second. The output power from the transmitter may be low and may be adapted to work at a maximum distance of 10 meters. The distance between the wireless communicable components in the apparatus of the present invention may however be variable from 1 cm up to 10000000 miles.

The components i), ii) and iii) may form an own entity as in the form of e.g. a thimble or a hand cuff which is further described below. The thimble or the hand cuff may then have a transmitter incorporated which may transmit signals to a receiver for further processing the signals to a quotient.

According to a preferred embodiment of the present invention the light beam of the apparatus is positioned essentially perpendicular to a measuring area of the vessel and is capable of emitting light of a wavelength where a minimal absorbance occurs on the red blood cells.

In the apparatus according to the present application at least one of the detectors may be capable of receiving transmitted light positioned essentially opposite to the light source and at least another detector may be capable of receiving reflected light and be positioned alongside the light source.

According to a preferred embodiment of the apparatus according to the present application the first detector, capable of receiving transmitted light, is positioned essentially opposite to the light source and the second detector, capable of receiving reflected light, is positioned alongside the light source.

According to a preferred embodiment of the apparatus according to the present application the apparatus may have the form of a finger or toe fitting test device equipped with the light source and the detectors.

The above test device according to the present application may according to a preferred embodiment comprise a thimblelike shell or a handcuff like shell, in short thimble or handcuff, which is preferably used for detection of blood characteristics including hemoglobin in fingers or toes, where at least one light source and the detectors are positioned as part of the thimble or hand cuff construction. The thimble embodiment may also be useful for detection of hemoglobin in paws on domestic animals.

The test device according to a preferred embodiment of the present invention may comprise a thimble-like shell to be applied on a finger or toe, the light source and the detectors being arranged to direct the light beam and detect the light intensity within the shell. This embodiment may have at least one light source and the detectors positioned in the shell cromprising a bend (constriction) whereby said light source and detectors are positioned and thus appearing in said bend (constriction), whereby said shell preferably is a part of a thimble construction for covering a finger or a toe.

The thimble embodiment and handcuff embodiment are essentially characterized by that it comprises at least one light emitting diod (LED) positioned on one side together with one detector and another detector essentially positioned perpendicular to the LED on the the other side.

These components are housed in the shell comprising:

a) a first part in close proximity to said components i.e. diode and detectors, which preferably houses the components in a rigid way.

b) an optional second part comprising a flexible material, preferably a polymeric material, most preferred silicon rubber; The first part comprises preferably a black plastic material, most preferred epoxy plastic or PMMA. The shell may be cast in industrial scale or may be hand made according to methods known to a person skilled in the art. When silicon rubber is cast to make the second part, preferably a colour powder (dye) is added to the rubber. The shorter the wavelength, the larger are the problems with external light, which thus may be minimized by adding dye to the material. Preferably the dye is black to minimize disturbances from other light sources. The shell may be fixed in a position on e.g. a finger or toe through that the first and second part are held together, preferably linked together by gluing the parts together or make the parts stick together in any other way. Further this shell forms an inward bend, an internal constriction, preferably the first part of the shell, where the finger or toe may be positioned during the measuring. The rigid and flexible parts may form a ring with a keyhole formed hole in the middle, with a bend, constriction, for squeezing e.g. a finger or a toe, partly or as a whole. The shell may have an arbitrary shape which surrounds said inward bend or constriction. In this way the finger may be "squeezed" so that a blood vessel is easily accessible for the measuring method according to the present invention. The finger may be sqeezed partly in order to have access to a suitable vessel. This squeezing may be acheived by mechanical means or by just pressing by hand. By using a clamping device which may comprise e.g. a rubber band together with a clamping ring, it may also be possible to fix the thimble and squeeze the measuring object.

The flexible material in the first part may also be made out of natural rubber or any pure flexible polymer or any co-polymer. The flexible material may also comprise one or more polymers. The materials in both parts do preferably not contain allergenic substances and thus the thimble is preferably well tolerable to the skin of a mammal. The shell allows for a finger or toe of a subject to be "sqeezed" so that a blood vessel is easily accessible for the measuring method according to the present invention. The blood vessel is preferably an artery or arteriol. The detection is preferably performed on a finger on the third phalanx.

The test device according a preferred embodiment of the present invention may comprise a thimble-like shell to be applied on a finger or toe, or a handcuff-like shell to be applied on a wrist, the light source and the detectors being arranged to direct the light beam and detect the light intensity within the shell. The test device according a preferred embodiment of the present invention may itself be shaped to fit a wrist, toe or finger.

Another preferred embodiment of the present invention is an apparatus having an additional light source, the light sources being adapted to appear on opposite sides of the vessel.

This further embodiment, the thimble, which is one preferred embodiment of the invention according to the present application is exemplified by a design which is described in example 3 in detail and also in FIG. 10 (scale 2:1) and 11. In the thimble embodiment, the distance between the light source(s) and the detector on the same side may be from 0.43 to 3.5 cm when referring from the centres of respective component, preferably it is from 0.87 cm to 1.75 cm. In FIG. 10 this is the distance between the components 1 and 2. The distance between the light source (s) and the detector appearing perpendicularly on the other side of the bend is from 0.37 to 3.0 cm, preferably it is from 0.75 cm to 1.50 cm when referring from the edge of each component which appears in the bend. In FIG. 10 this is the distance between the components 1 and 3. Preferable the components are fixed to the edge of the bend, which may house a finger or a toe. The thimble according to one embodiment of the present invention may be present wherein the rigid and flexible parts formes a circular ring with a keyhole formed hole in the middle, with a bend for e.g. a finger or a toe. This cylinder forming a keyhole in the middle, for receiving (and covering) a finger or a toe, may have a height of from 0.72 to 5.8 cm, preferably from 1.45 cm to 2.9 cm. The ring (cylinder) may have a diameter from 0.77 to 6.2 cm, preferably from 1.55 to 3.1 cm.

The vessel in which the blood characteristics is to be monitored may be identified by proper choice of the separation between the light source(s) and the detector(s). The theoretical analysis and experimental verification of this optical technique has been presented by I. Fridolin, K. Hansson and L.-G. Lindberg in two papers which have been accepted and are to be published in Physics in Medicine and Biology (Optical non-invasive technique for vessel imaging I and II, Department of Biomedical Engineering, Linkoping University, Sweden). The following is a summary of their analysis and experimental verifications.

Light reflection from human tissue depends on many parameters, such as optical wavelength, source-detector separation, size and aperture of the light source and detector and optical properties of the blood and tissues. The separation between the light source and the detector fibre was varied between five centre-to-centre distances: 2, 3, 4, 5 and 6 mm. The analysis agreed with the earlier conclusion that to increase the influence from deeper tissue on the measured signal, a larger light source-detector separation should be selected.

The resultant mathematical analysis and verified experimental results can be summarized as:

At larger separation values the photons forming maximum photon paths and detected by the photodetector originate from deeper layer than for short separation values. This is illustrated in FIG. 14. FIG. 14 is a schematic diagram of photon migration at two different source-detector separations and for different FL ($\alpha$) (FL(0) and FL($\pi/2$)). FL=fibre pair position relative the Lining of the vein. Two positions of the light source and the photodetector fibres relative to the lining of the vein were considered. An angle $\alpha$ is defined to characterize different positions. The abbreviation FL(0) means that the light source and the photodetector are positioned in parallel and FL($\pi/2$) that the light source and the photodetector are positioned perpendicular to the vessel. Monte Carlo simulations have shown that for human tissues in the near infrared region photons penetrate approximately 2 mm before being detected if the separation is about 2 mm between the source and the detector.

The blood vessels in terms of veins may further be determined at three vascular levels in combination with a fixed fibre diameter (1 mm) using the probe and technique above summarized and according to;

a superficial vascular level (approximately 1 mm). This may be sufficient to set the minimal distance between the illuminating and detecting fibre (2 mm during the above experiments.

an intermediate vascular level (approximately 2 mm). The minimal distance between the illuminating and detecting fibre may preferably be 2–3 mm a deep vascular level (approximately 3 mm). The distance between the illuminating and detecting fibre may preferably be greater than 3 mm.

The result of this above summarized research in the above referenced papers makes it possible to determine blood characteristics and physiological parameters, such as blood flow, blood constants and oxygen saturation, on a selected vascular bed in veins or arteries. If wrists (containing Radialis) or thicker parts of the body, like upper parts of the arms, are to be measured, when regarding blood characteristics including Hb, the above distances between the fibres (light source and detector) may be from 6 to 12 mm. For thicker parts (like arms containing Brachialis) of the body the distance may be from 12 to 30 mm. When measuring on wrists or thicker parts of the body a pressure may preferably be put on the measurement locus. The method according to the present invention may further be used when measuring on vessels situated below the ankles (containing dorsalis pedis). Thus the present invention may have light source(s) and detector(s) on different distances as set out above depending on which measuring area is to be monitored, which enables reaching the aimed vessel and thus the detection of the blood characteristics including Hb. The distance between detector(s) and light source (a) may, as set out above, thus be from 1 to 20 mm depending on the measuring area.

The theoretical solution for light distribution in tissue, described in paper II above, may be the base for describing how hemoglobin can be measured in reflection mode. Equation 32 provides a general solution in which equation $\mu_a$ and $\mu_a$ describes the influence of the optical coefficients and H and B (or Z) the influence on pulsative variations in vessel diameter during the cardiac pulse. The light source(s) is (are) connected by cords to any power source, which may be an oscillator or a battery. The oscillator may be connected to amplifiers and LED-Drivers. These drivers may be connected to one or more LEDs. Detectors, e.g. photodiodes for transmission and reflection, respectively, are connected to at least one current/voltage converter, which in turn may be connected to the amplifiers. The signals may then pass to Band pass Filters and subsequently to analog outputs or to a $\mu$-controller which is connected to a Read out unit.

The apparatus according to the present application may according to an additionally preferred embodiment have at least two light sources which are positioned and thus appearing on two different opposite sides of the measuring object during detection. Preferably the light sources are not directly opposite each other. This positioning may, in a preferred embodiment of the present invention, be part of a thimble construction. Apparatuses according to the present invention may be singular or big matrix probes comprising several light sources and detectors which may have the form of a ring, plate, cube, sphere.

The apparatus according to the present application may according to an additionally preferred embodiment be comprised in a dialysis apparatus, preferably for performing hemodialysis.

The apparatus according to the present application may according to an additionally preferred embodiment have at least two light sources which are positioned and thus appearing on a common side of the measuring object during detection. When two LEDs are used they are preferably interchangable with each other. The LEDs may be present in the same electronic chip.

The apparatus according to the present application may according to an additionally preferred embodiment have two light sources which are positioned and thus appearing on the same common side of the measuring object during detection, where one light source (preferably a LED) emits green light and the other light source (preferably a LED) emits NIR light of from 770 nm to 950 nm. The two light sources direct two light beams against the same side of the vessel, one of the light beams having from 770 nm to 950 nm and the other light beam having a wavelength of from 480 to 590 nm. Preferably the green light is emitted in the green wavelength range i.e. 480–590 nm, most preferred at approximately 500 nm.

The apparatus according to the present application may according to an additionally preferred embodiment have two light sources directing two light beams, preferably essentially in parallel with each other, against the same side of the vessel wherein the first light source emits light at a wavelength which is relatively not absorbable by red blood cells, and the second light source emits light of a wavelength which is relatively absorbable by the red blood cells.

By directing two light beams with a wavelength <1500 nm a better sensitivity of the method may be obtained. In this above preferred embodiment of the present invention one light beam has a longer wavelength, preferably NIR (Near InfraRed) light, and the other has a shorter wavelength preferably in the range of 200–580 nm, most preferred green light. Using green light in the other light source is advantageous because green light is heavily absorbed by red blood cells.

The processor for calculating a quotient of said intensity of said transmitted light detected by said first detector and said intensity of said reflected light detected by said second detector and for analyzing said quotient to determine the blood characteristics including hemoglobin may be included in a computer. Further, the registration means may also be included in a computer. The visualization may be accomplished by any visualization means, but is preferably accomplished by using a computer display and/or a printer device. The processing of the data obtained during the measurement may also include quotient forming of reflection/transmission, transmission/rerlection with or without AC and/or DC with or without multiplying of one or more of the obtained data in order to compensate for variations in volume or flow. There may also be included a computer program in the processor for search for the optimal measuring spot, especially when using a matrix comprising several light sources and detectors, for controlling/verifying reliable strength of the signal, for performing algorithm calculations, for evaluating data against stored standard curves, for displaying (and storing) the results together with patient data and relevant quality criteria. The output of the results from measuring using the present invention may be accomplished on a connected printer device, optionally connected via the visualization means.

For the performance of the method according to the invention a calibration curve may be used. This calibration curve stored in a memory of a processor, which preferably is part of a computer, allows the readily conversion from the quotient reflection/transmission %, which may be stated: $AC_R/AC_T$ or $DC_R/DC_T$, obtained when directing light beam and subsequently detecting the reflection and transmission, to a hemoglobin value in mmol/l. The calibration curve may preferably be obtained by analysing in parallel with the method according to the present invention, drawn blood samples from volontary healthy persons and patients on a Hemocue apparatus or blood gas analyser. A spectrophotometric absorption curve in reflection mode or recording curve in reflection mode may also be used in conjunction with the method above.

Of course, it may be possible to process the reflection and transmission signals in a manual way and hereby determine the blood characteristics including hemoglobin. The results may also be visualized in a manual way by e.g. plotting the results in a diagram. Thus manually comparison of a calibration curve and the curve for the result(s) may also be done. The signals detected by the detectors may further preferably be analysed using the following procedure:

As the PPG-signal is consisting of two parts, a constant signal and a pulsating signal superposed on the constant signal, first maximum and minimum points are calculated. The maximum points are calculated through sweeping a window over,the curve. The size of the window is adjusted according to the frequency of the AC-signal (the pulse) to approximately 60% of the period time, divided equally to the right and to the left. If no value within the window is higher than the value in the middle, this value is designated a maximum point, whereafter the window is moved by leaps half of the window length in order to avoid that a plateau formed curve is registrated as many maximum points. If any value within the window exceeds the value in the middle, the window is moved only one step. In a corresponding way the minimum points are calculated.

For each minimum point an AC-height is calculated as the height to the connection line between the maximum points closest to the left and to the right of the middle point, respectively, taken from the in between laying minimum point. Of nine subsequently following AC-heights, the median height is selected as the representative of the AC-signal, in order to filter away artefacts that may give rise to erroneously detected minimum or maximum points. The DC-signal is then calculated as the total height to the minimum point that laid basis for the AC-signal, plus the AC-signal. FIG. 18 shows an example of the above procedure. Step d) in the summary of the invention above may preferably comprise the following steps:

I) sweeping a window over a curve with detected values from transmission and/or reflection, wherein the size of said window preferably is approximately 60% of the period time, divided equally to the right and to. the left;

II) if no value within said window is higher than the mean (middle) value, the value is designated a maximum point whereupon the window is moved by leap half of the window length, or if a value exceeds the middle value the window is moved only one step;

III) the minimum points are designated accordingly in the same manner as in II) but with regards to minimum values instead of maximum values;

IV) the height of the AC-signal is obtained by subtracting from a value on a connection line involving two maximum points, the vertically lying value of an in between lying minimum point;

V) repeating step IV) at least 8 times, and summarize the values from IV) and dividing the sum with number of observations, thus obtaining a median AC-value VI) optionally obtaining the DC-signal by adding the total height of the minimum point in IV) to the median AC-signal of step V). Preferably these above steps are accomplished by using a computer program for obtaining said AC-signal and optionally said DC-signal. Preferably the computer program is stored on a data carrier for performing the above steps I) to VI) Preferably the data carrier is part of the processor (or central processing unit, CPU) designated iv) of the Summary of invention part above or a separate floppy disc to be inserted and used by the processor. The processor may preferably comprise a computer program for performing the method according to the present invention, as e.g. set forth in the summary of the invention, and/or the above steps I to VI.

Another embodiment of the present invention is also a computer program stored on a data carrier for performing the method according to the present invention, as e.g. set forth in the summary of the invention, and/or the above steps I to VI.

When measuring on the skin the equation looks similar except that the light may be reduced depending on the absorption of light and the light scattering in the tissue. The intensity may be compensated at different blood flows when performing the current invention, the method and using the apparatus. When performing skin measurement, this is preferably performed over a large blood vessel, e.g. on the finger of the third phalanx. The blood vessel must however contain a blood volume which markedly differs from the blood volume in the surroundings (which may comprise capillaries). It should be noted that the method and apparatus according to the present invention may preferably be used for measuring the central blood characteristics as represented in larger vessels such as arteries. This may be achieved by compensating for the influence of blood pressure and blood flow on the measured intensities by taking the quotient between the reflected and transmitted light. The effect used in the present method and apparatus according to the present invention may also be used for measuring the change in blood characteristics in one individual or in an extracorporeal system when the blood haemoglobin value is constant. This is further illustrated in example 4 where this was performed by using an apparatus according to the present invention. Using the method it is thus possible to follow changes in blood volume and pathological changes in the body.

A further feature of the present invention is that the method and the apparatus may in a very simple way be adapted to detect oxygen, as 97–98% of all oxygen in the blood of a human being is transported by hemoglobin-molecules in the blood. Of course the method may also be used for detecting red cells themselves asihemoglobin it normally incorporated in the red blood cells, unless they are lysed. As the viscosity of blood corresponds to the amount of red blood cells in the blood, the method may also be used for detection of viscosity as well. The method and apparatus according to the present invention may also be used to determine the hematocrit (Hct) The difference between hemoglobin (which is the grams of hemoglobin per volume of blood) and hematocrit (which is the volume of blood cells per volume of blood) is determined by the concentration of hemoglobin within the cells which determines the index of refraction of the cells.

Several different blood constants are used in diagnostics. Some are interchangeable and there are generally accepted relationships between these. The generally accepted relationships are:

| Constant | Measures | Calculation |
|---|---|---|
| RBC | number of red blood cell per | |
| EPC | unit volume of blood or erythrocyte particle concentration | |
| Hb | concentration of haemoglobin in blood | |
| Hct | hematocrit or erythrocyte | Hct = RBC × MCV |
| EVF | erythrocyte volume fraction. Fraction of red blood cell volume of total volume. | |
| MCV | erythrocyte volume, abr. mean corpuscular volume | MCV = EVF/RBC |
| MCH | weight of haemoglobin in erythrocytes abr. mean corpuscular haemoglobin | MCH = Hb/RBC |
| MCHC | concentration of haemoglobin in erythrocytes, abr. mean corpuscular haemoglobin concentration | MCHC = Hb/EVF |

Further, human blood is made up of formed elements and plasma. There are three basic types of formed blood cell components: red blood cells, white blood cells (leukocytes) and platelets. The red blood cells contain hemoglobin that carries oxygen from the lungs to the tissues of the body. Normally the hemoglobin concentration varies between 132–163 gram/litre in men, and 116–148 gram/litre in women. The hematocrit (Hct) normally varies between 39–49% (EVF 0.39–0.49) in men, and 37–44% (EVF 0.37–0.44) in women. White blood cells are of approximately the same size as red blood cells, but they do not contain hemoglobin. A normal healthy individual has approximately 5,000,000 red blood cells per cubic millimeter of blood (the human body contains approximately 5 litres of blood), and approximately 7,500 white blood cells per cubic millimeter of blood. Therefore, a normal healthy individual will have approximately one white blood cell (leukocyte) for every 670 red blood cells circulating in the vascular system. The white blood cells (TBCs) are responsible for the immune system in a mammal, preferably a human being. E.g. certain WBCs engulf intruder agents.

Concerning platelets, they are the smallest of the formed blood cell components, being typically less than 1 μm in diameter. Platelets are less abundant than red cells, but more abundant than white blood cells. A normal healthy individual has approximately one platelet for every 17 red blood cells circulating in the vascular system for a total of about two trillion.

In summary, the method and apparatus according to the present invention may be used to determine various characteristics of the vascular system through the use of known relationships between parameters, as for the cases when determining indirectly the amount of white blood cells and/or platelets. (For WBCs the factor is 1/670 of the red blood cells and for platelets it is 1/17). Thus the blood characteristics in steps e) and iv) in the method and apparatus, respectively, according to the invention also include white blood cells and/or platelets. Cholesterol and albumin concentration may also be determined when using the known hemoglobin concentration in connection with the method described in GB 2 329 015, hereby incorporated by reference. The above method refers to non-invasive measurement of blood component concentrations.

The method and apparatus according to the invention also enables diagnosing of irregularites or diseases in a mammal e.g. anemia where there is a shortage of red blood cells. Bulimia patients often suffer from anemia. Further, the method and the apparatus gives an indirect possibility of measuring platelet diseases such as thrombocytopenia. This could be indicative for problems of menostasis and coagulation. An elevated level of certain white blood cells is further indicative of a viral infection. Leukocytosis and leukopenia are also thinkable indications which may be possible to detect indirectly. Other diseases of the phagocytic and Immune Systems may also be detectable. Neonatal monitoring is another application area for the present invention. Operative monitoring is also a conceivable application. The apparatus may be set to a "zero-level" at the start of an operation, in order to compensate for stable interactive effects (skin colour, lipids and so on) and thus a readily monitoring of blood characteristics including hemoglobin may be acheived.

The current invention, the method and apparatus, also enables an accurate measurement of patients blood, without any risks associated with drawing blood (e.g. AIDS, hepatitis A, B and C etc). Drawing blood by using injection needles is also a painful method, especially for individuals requiring many blood samples to be drawn. These drawbacks may be eliminated by using the method and apparatus according to the present invention. Further the method and apparatus according to the present invention is especially suitable for measurements on children.

The present invention also refers to use of an apparatus according the present application in a dialysis apparatus (or dialysis device).

The examples which follow illustrate embodiments of the present invention, but are not intended to limit the scope in any way.

The numbers in the figures have the following explanations:

1. Green Light Emitting Diode (LED) and NIR LED; they are interchangable
2. Detector
3. Detector
4. Second part comprising a stiffer material
5. First part comprising a flexible material The A—A, B—B, C—C are sections of the thimble.

Figure 11:
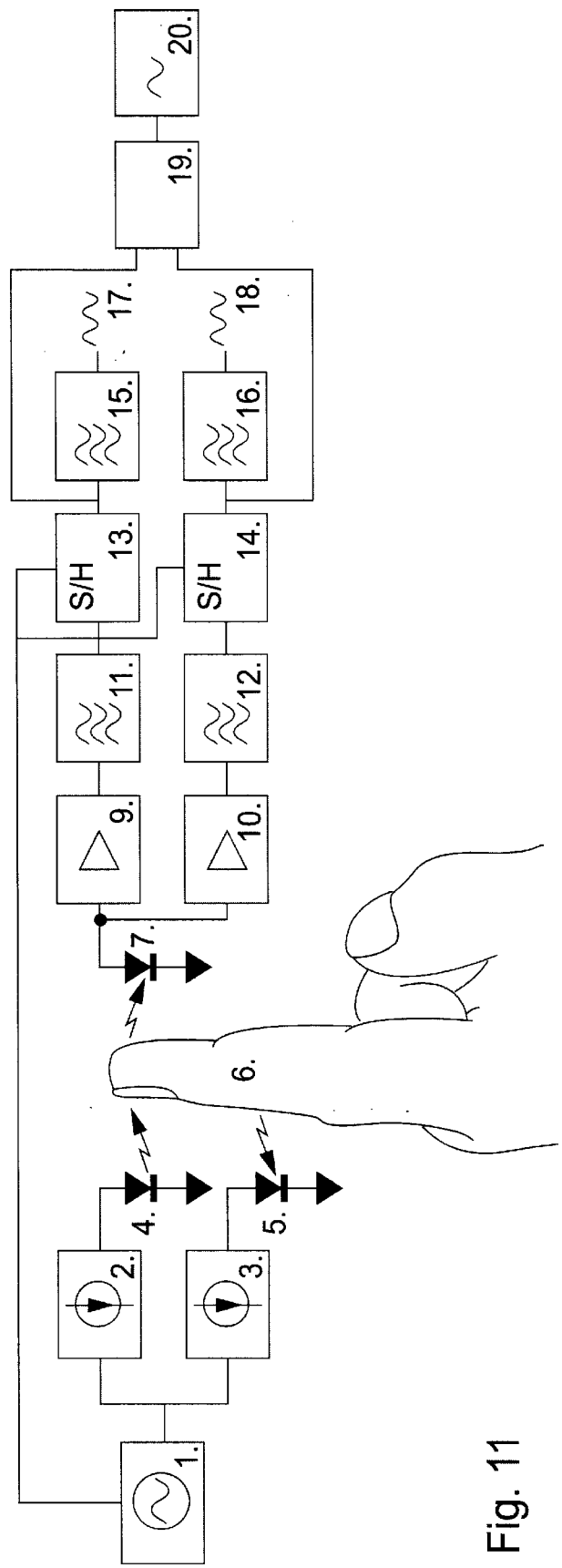
Figure 12:
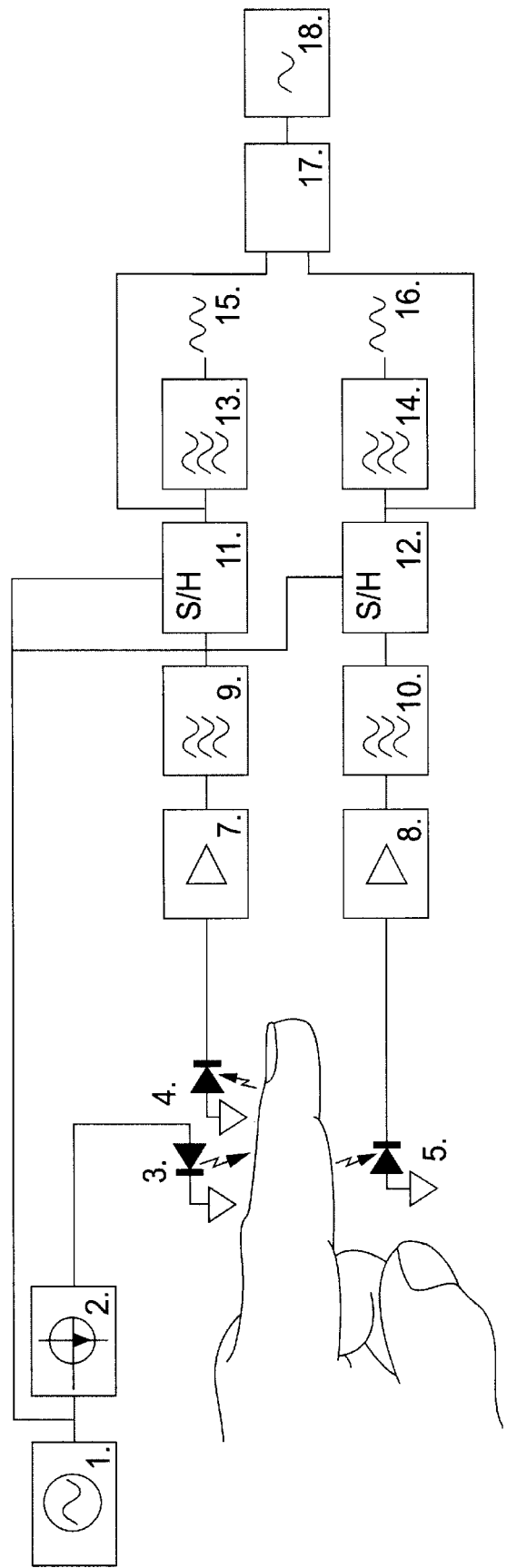

FIG. 11 shows a block diagram illustrating schematically how the thimble (the shell is not shown; only light sources and detectors is shown) is connected. The numbers in the figure has the following explanations:

1. oscillator
2. LED-Driver λ1
3. LED-Driver λ2
4. LED λ1 or 2
5. Photodiode reflection
6. Subject
7. Photodiode transmission
9. Currentvoltage converter
10. Current/Voltage converter
11. Lowpass Filter
12. Lowpass Filter
13. Sample and Hold amplifier
14. Sample and Hold amplifier
15. Band pass Filter
16. Band pass Filter
17. Analog output
18. Analog output
19. μ-controller
20. Read out unit FIG. 12 shows a block diagram illustrating schematically how the thimble (the shell is not shown; only light sources and detectors is shown) is connected in another embodiment of the thimble. The numbers in the figure has the following explanations:

1. oscillator
2. LED-Drivers
3. LED

Figure 13:
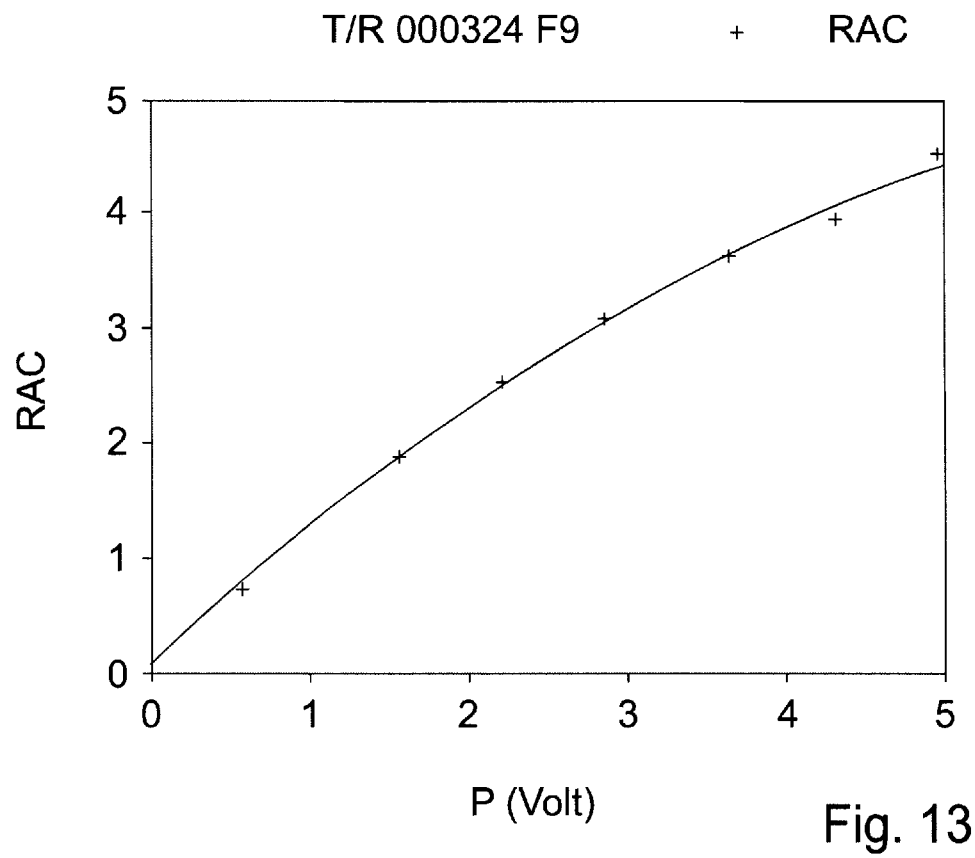

4. Photodiode reflection
5. Photodiode transmission
6. Subject
7. Current/Voltage converter
8. Current/Voltage converter
9. Lowpass Filter
10. Lowpass Filter
11. Sample and Hold amplifier
12. Sample and Hold amplifier
13. Band pass Filter
14. Band pass Filter
15. Analog output
16. Analog output
17. μ-controller
18. Read out unit FIG. 13 shows the intensity of the reflected pulsative light versus increasing systolic pressure.

Figure 14:
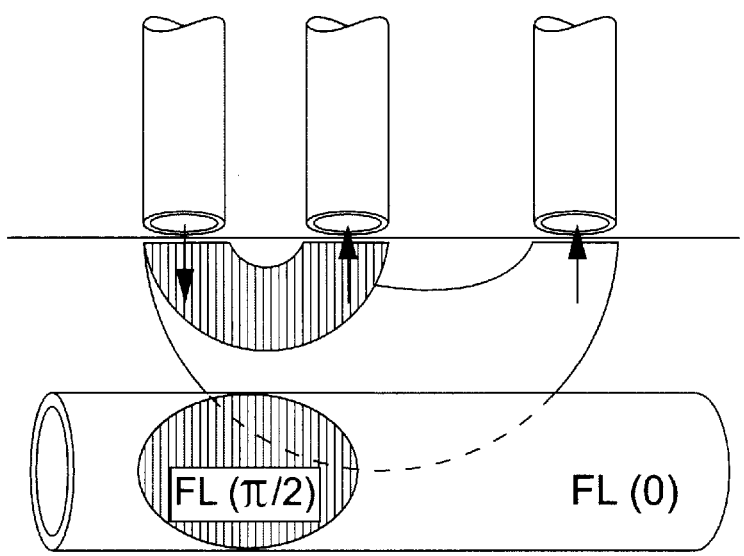

FIG. 14 shows at larger separation values the photons forming maximum photon paths and detected by the photodetector originate from deeper layer than for short separation values.

Figure 15:
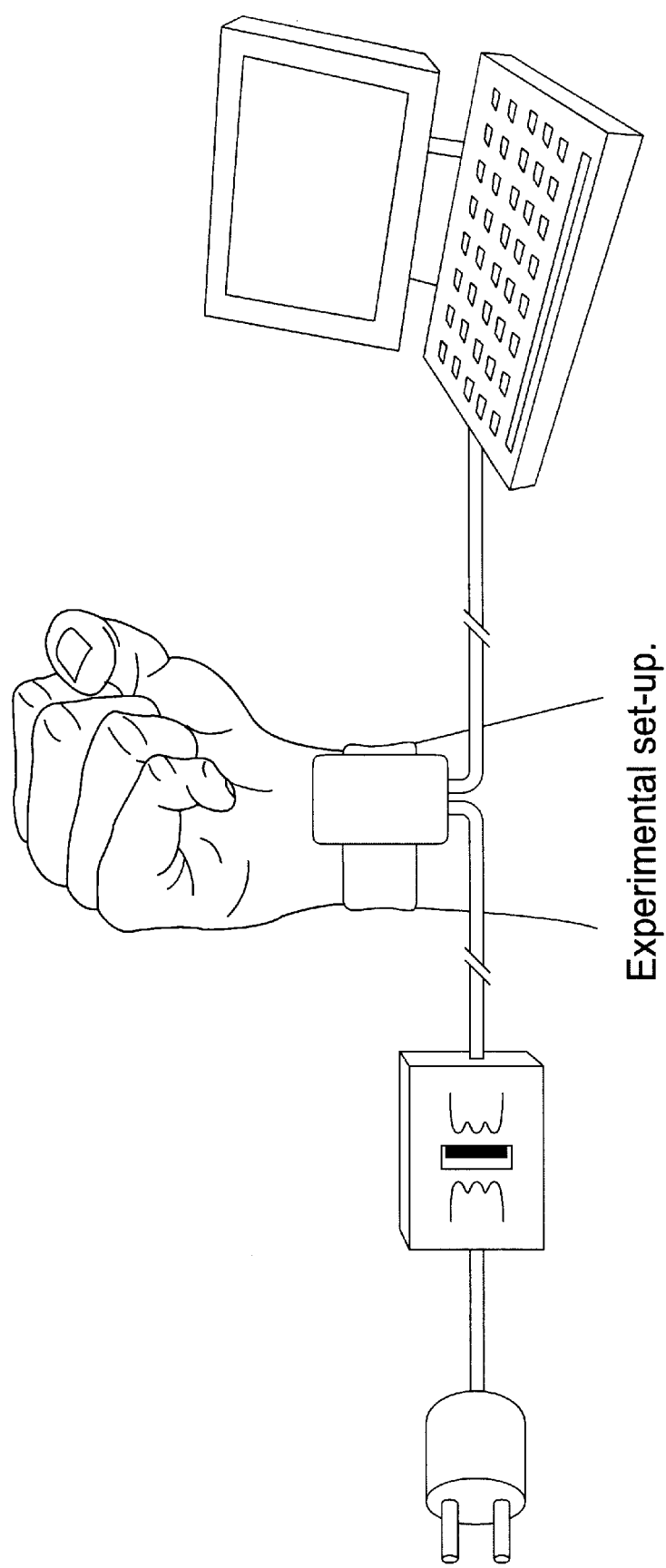

FIG. 15 shows a-probe, where only reflected light was detected, fastened on the wrist of a subject. The probe was placed on the wrist over the radial artery.

Figure 16:
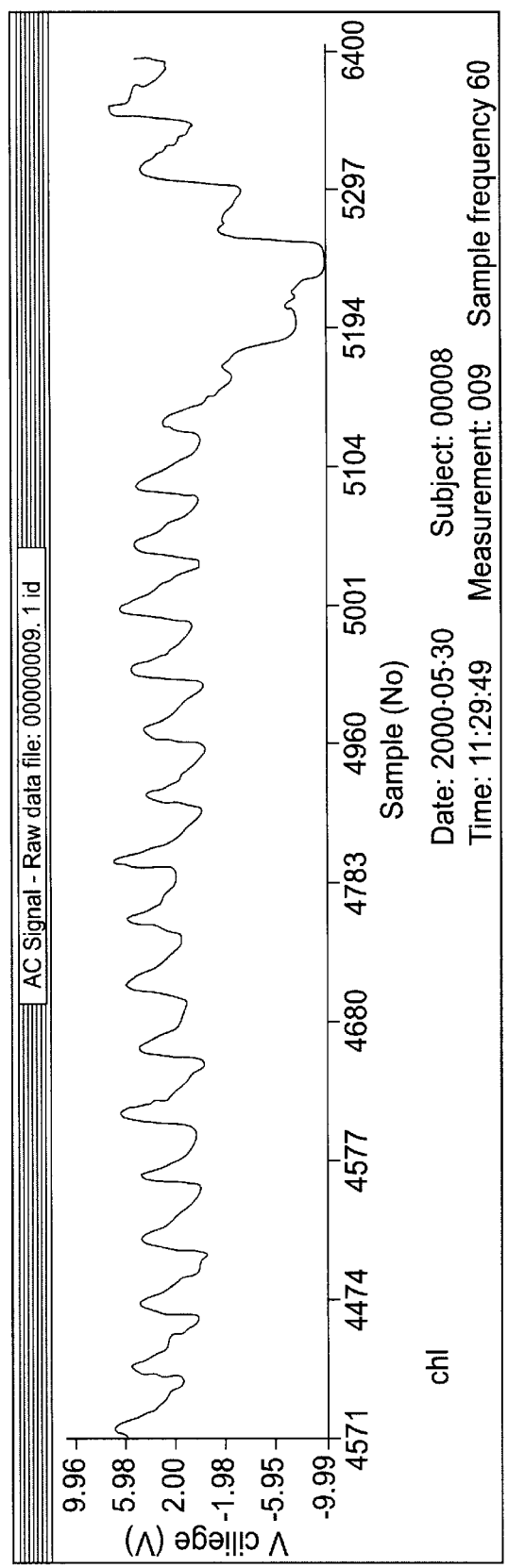

FIG. 16 shows when saline was injected in the flow direction close to the probe in FIG. 15. Only the intensity of the reflected light was recorded and the change in signal corresponded to the dilution effect in the blood.

Figure 17:
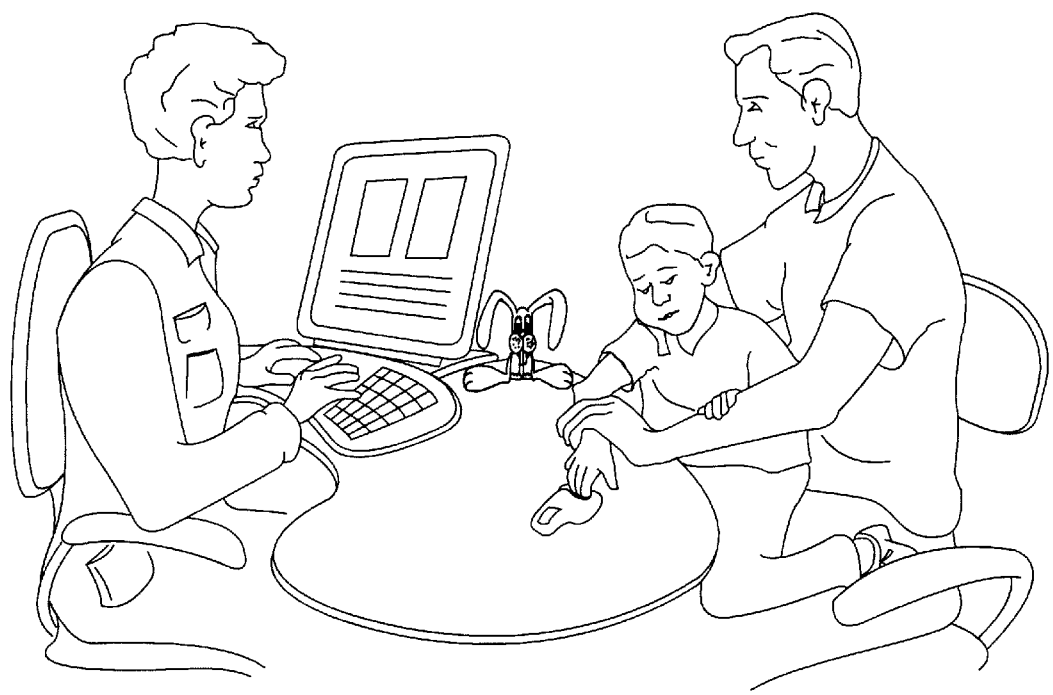

FIG. 17 shows a system including a computer and a blood characteristics-apparatus where there is no need for cables between them when using the Bluetooth™ technology.

Figure 18:
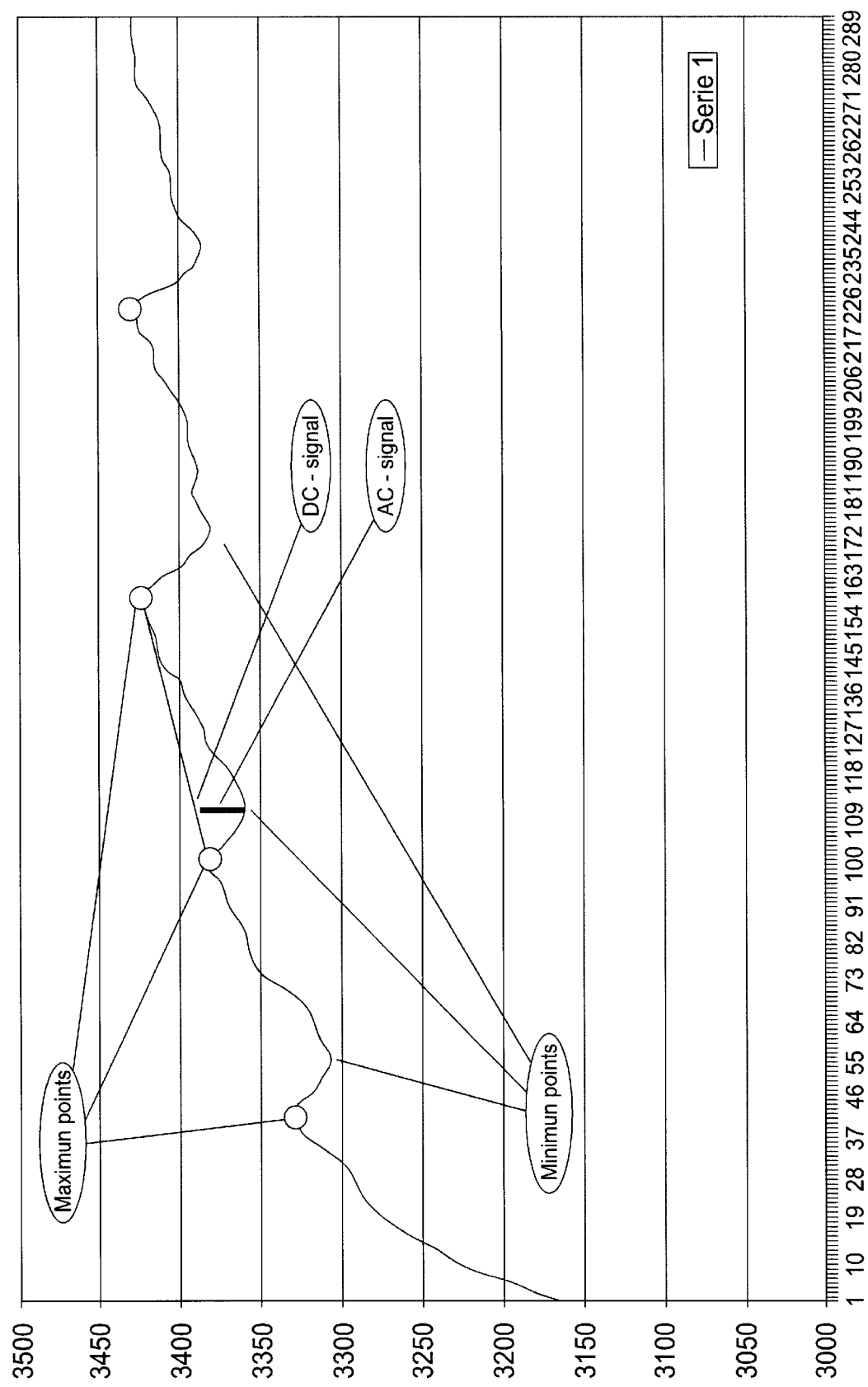

FIG. 18 shows the PPG-signal with DC-signal, AC-signal, minimum points and maximum points.

EXPERIMENTAL DETAILS

EXAMPLE 1

Detection was performed using the following equipment:

A tube of acrylic glass (PMMA) with an inside diameter of 3 mm

Two optical fibres with a diameter of 0.094 mm. One fibre was for transmission of light (light source) and the other for receiving reflection of light (photo detector).

A glass tube with an outside diameter of 0.210 mm for housing the optical fibres placed in parallel with each other.

Whole blood from volonteers, which was pumped through the tube made up of PMMA.

Figure 1:
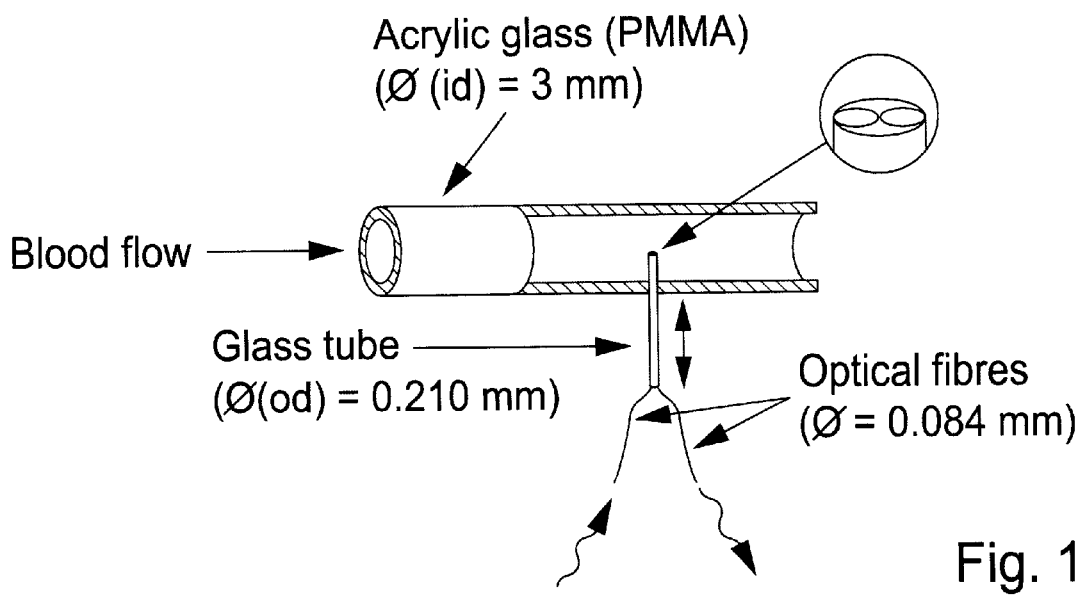
FIG. 1 shows schematically a flow model for detection of light reflection.
Figure 2:
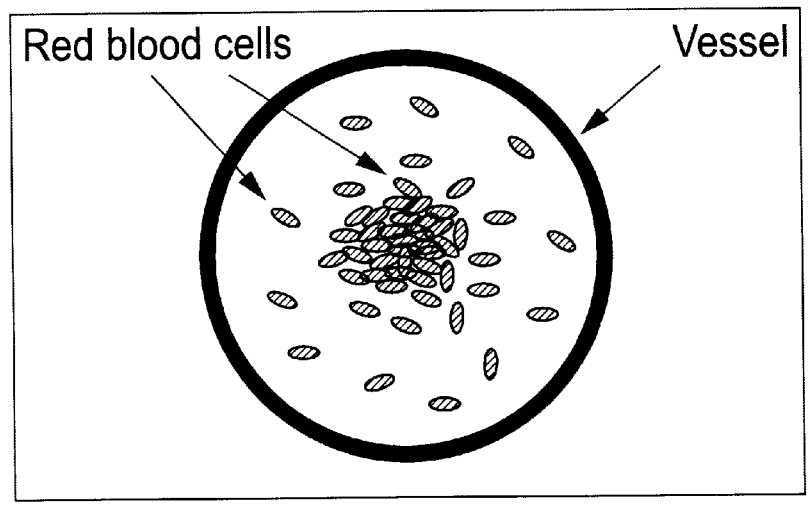
FIG. 2 shows the orientation of red blood cells at an intermediate or high level of shear rate or blood flow.
Figure 3:
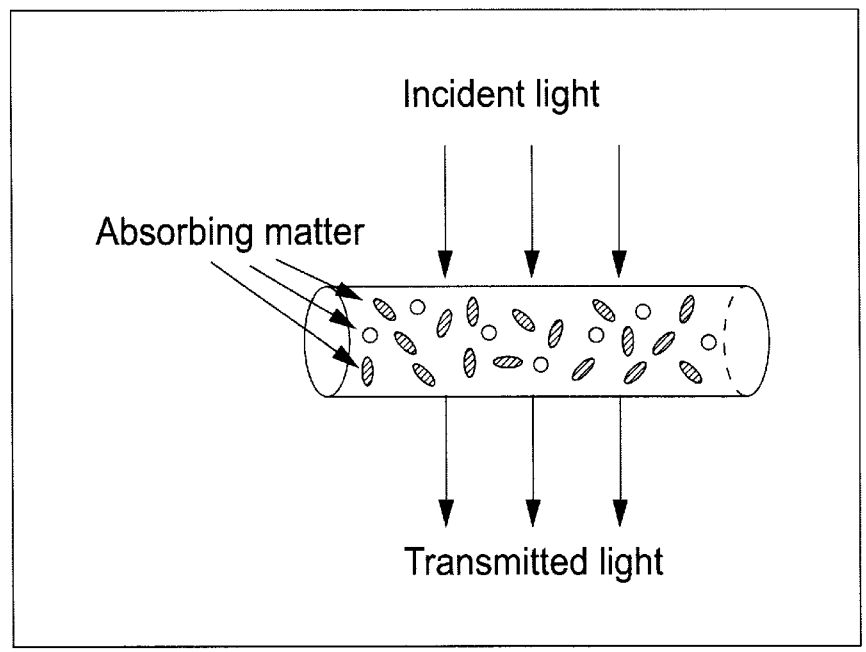
FIG. 3 shows light.absorption in blood due to different absorbing matter.
Figure 4:
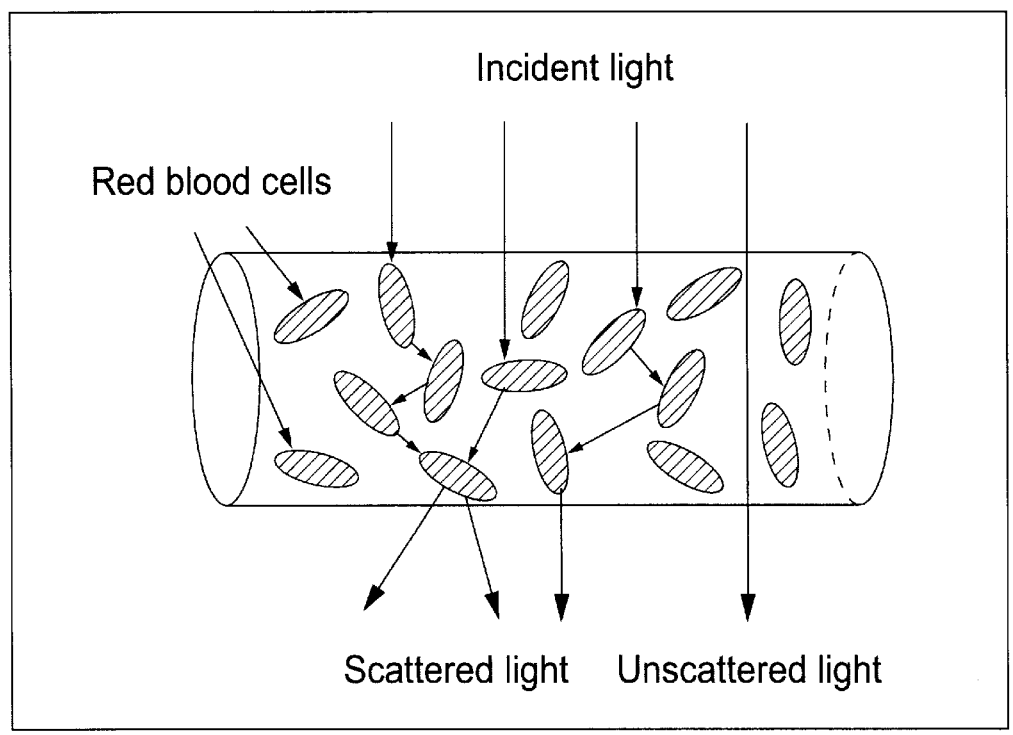
FIG. 4 shows light scattering due to red blood cells.

FIG. 1 shows schematically the flow model for detection of light reflection. FIG. 2 shows the orientation of red blood cells at an intermediate level of shear rate. FIG. 3 shows light absorption in blood due to different absorbing matter. FIG. 4 shows light scattering due to red blood cells.

The results from this experiment suggest that the light is spread in a special way when hitting the red blood cells in the tube. This probably depends on the shape of the blood cells, bi-concave disc, which forces the cells to orientate in different way as they move in the circular tube. This is demonstrated with optical technique through placing two optical fibres in a small catheter, where one of the fibres works as a light source and the other as photodetector as set out above. The fibre pair is moved from one periphery to the other in a cross-section of a circular tube.

Figure 5:
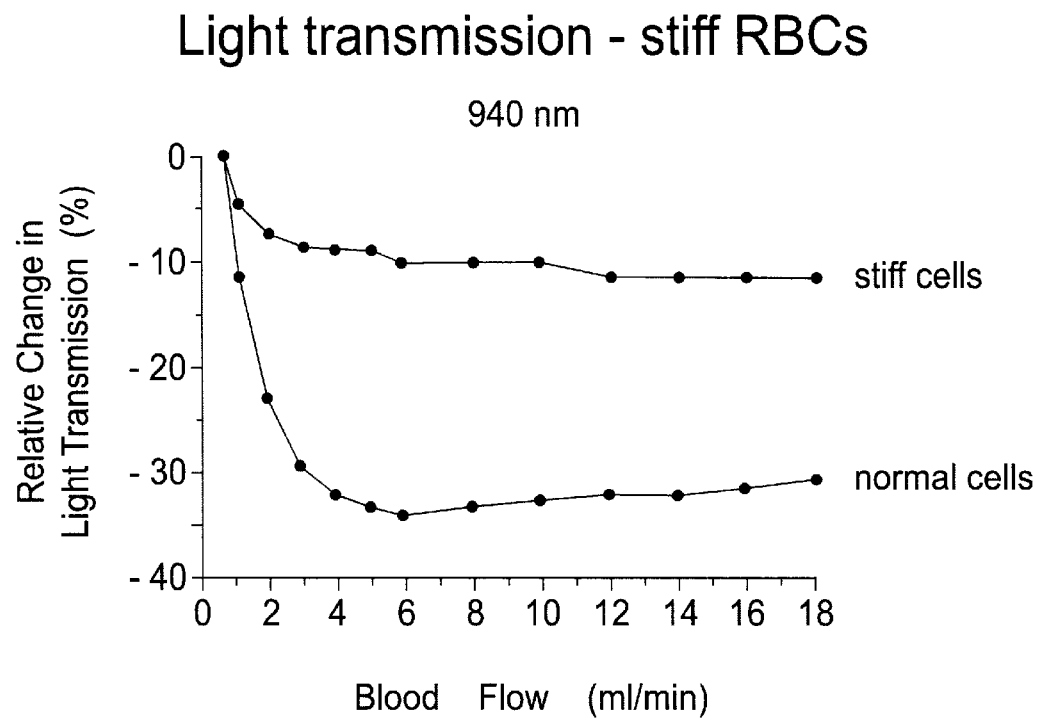
FIG. 5 shows the relative change in transmitted light versus blood flow for two different types of red blood cells.
Figure 6:
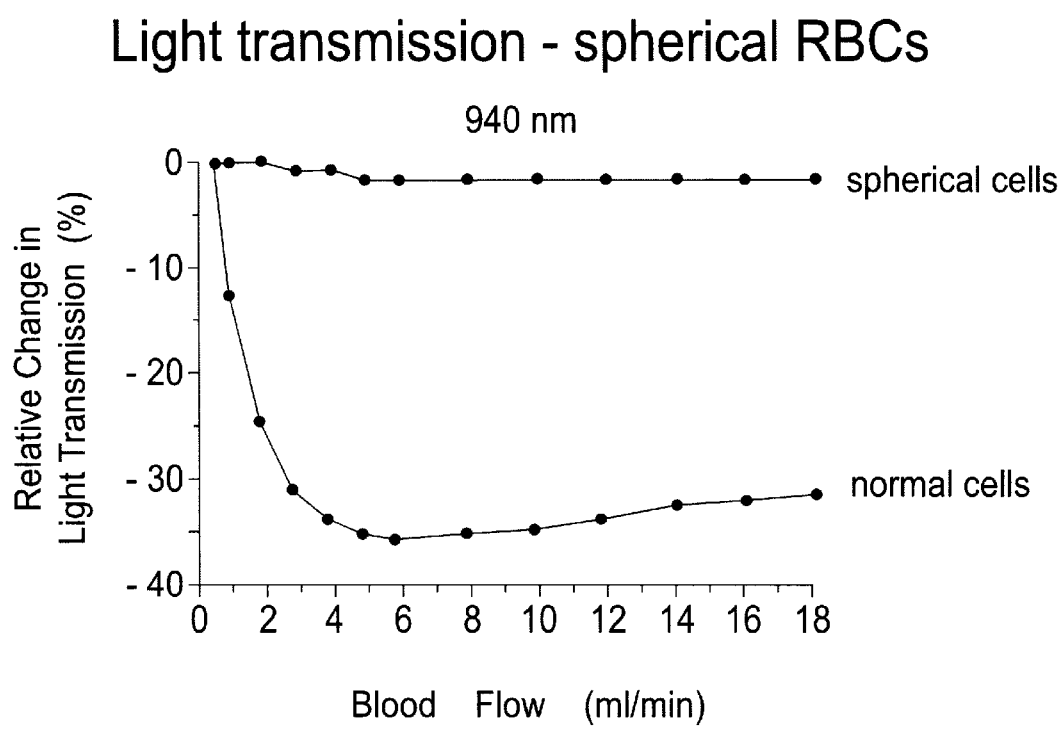
FIG. 6 shows the relative change in transmitted light intensity versus blood flow for two types of blood cells.

FIGS. 5 and 6 are summaries of experimental results. The intensity of the light transmitted from the red blood cells flowing through a tube of acrylic glass. The experimental setup was the same as in the above mentioned experiments.

FIG. 5 shows the relative change in transmitted light versus blood flow for two different types of red blood cells. The "stiff cells" are red blood cells, which were treated with glutaraldehyde in order to make them stiff i.e. they had lost their ability to change shape with the stress created by the flow.

The results show that one important characteristic of the red blood cells is their flexibility. This results in a change of shape—elongation—and orientation with increasing flow as demonstrated by the reduced transmission intensity with increasing flow. Red blood cells without this flexibility (stiff) show little or no orientation effect with flow as measured with light transmission change.

FIG. 6 shows the relative change in transmitted light intensity versus blood flow for two types of blood cells. The "spherical cells" are red blood cells treated with non-isotonic buffer solution. This makes the cells loose their bi-concave disc shape. This results in a close contact and orientation with increasing flow as demonstrated by the reduced transmission intensity with increasing flow. Red blood cells with spherical shape exhibit less shear stress with increasing flow and show little or no orientation effect with flow as measured light transmission changes.

We can thus conclude that the cell orientation of the red blood cells as a function of flow e.g. flexible or inflexible tubes or arteries in humans and mammals is mainly due to their unique bi-concave disc shape and flexibility.

EXAMPLE 2

Figure 7:
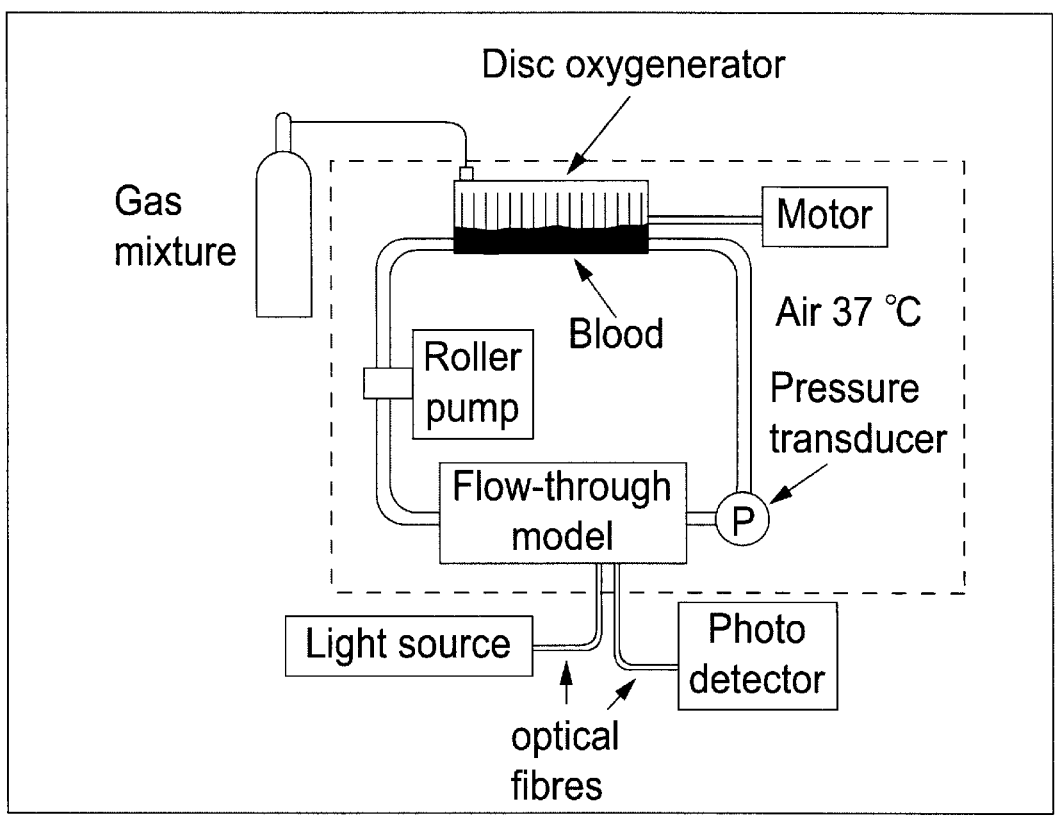
FIG. 7 shows essentially the experimental setup of an example (example 2).

A second experimental setup consisted essentially of the following. There were essentially three main parts:

a cylindrical disc oxygenator which also served as a blood reservoir.

a flow controlled roller pump (peristaltic pump)

a rigid flow-through model connected to a light source and photodetectors via optical fibres The setup is essentially shown in FIG. 7, but it lacks one photodetectot, as both transmission and reflection was measured. A waveform generator regulated the roller pump, which produced a continuous blood flow. A pressure transducer was also part of the circuit for the blood flow. The blood temperature was maintained constant at 37.0°±0.1° C., by circulating warm air around the setup.

A gas mixture was lead into the reservoir and mixed with the blood. The gas exchange was simulated by a disc oxygenator and the gas mixture consisted of 19% oxygen and 5.6% carbon dioxide in nitrogen. The oxygen saturation was maintained at 98–99%, and the blood gas parameters ($pO_2$, $pCO_2$ and pH) were assumed not to deviate from normal physiological values.

Laminar flow-through model was used in order to minimize hemolysis of the red blood cells. The wavelength that was used was 800 nm, an isobestic point where a minimal absorbance of light take place on the red blood cells. The measurements were performed on a tube made of acrylic glass with an inner diameter of 3.0 mm.

Figure 8:
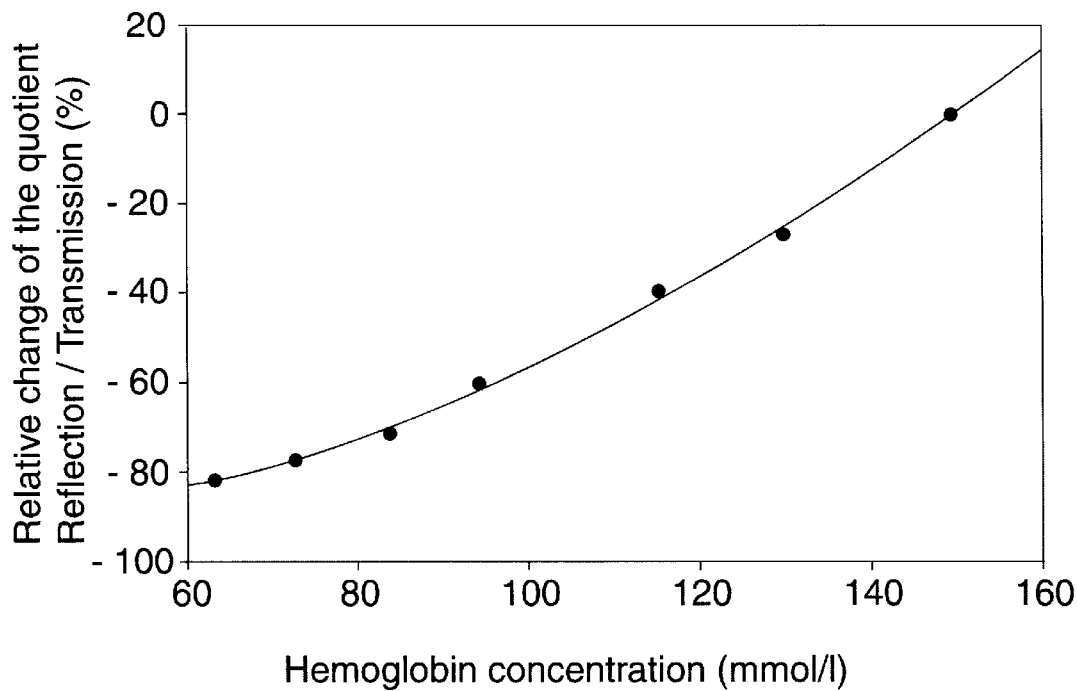
FIG. 8 shows a diagram with the relative change of the quotient reflection/transmission (%) i.e. $AC_R/AC_T$ on the y-axis and the hemoglobin concentration in mmol/l on the x-axis.

FIG. 8 shows a diagram with the relative change of the quotient reflection/transmission (%) i.e. $AC_3/AC_T$, on the y-axis and the hemoglobin concentration in mmol/l on the x-axis. The quotient between reflection/transmission appears to be independent of the blood flow, but appears to vary according to the concentration of hemoglobin. The optically registered hemoglobin (Hb) signal may thus be stated;

$$Hb = AC_R/AC_T$$

and this has been confirmed by analysing in parallel with the method according to the present invention, drawn blood samples from volontary healthy persons and patients on a Hemocue apparatus (Angelholm, Sweden) in a Clinical Chemistry Laboratory. Thus a calibration curve was obtained. This calibration curve may be stored in a memory of the processor, which preferably is part of a computer, which allows readily the conversion from $AC_R/AC_T$, obtained when directing light beam and subsequently detecting the reflection and transmission in accordance with the method of the invention, to a hemoglobin value in mmol/l. This curve may be linear at certain conditions.

Figure 9:
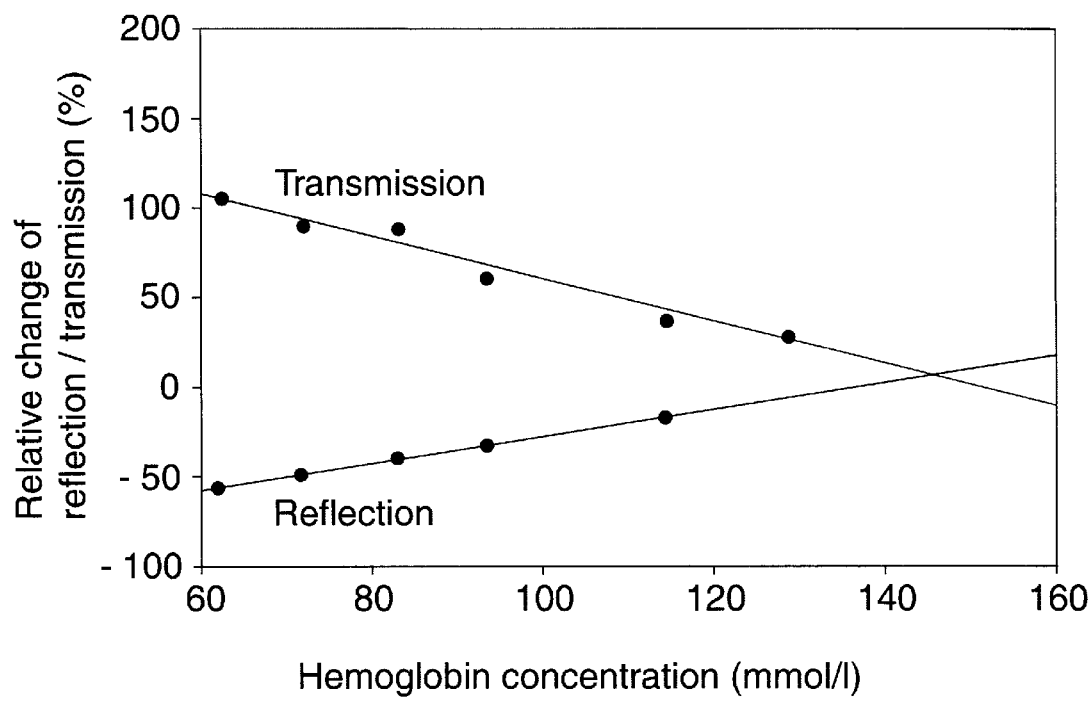
FIG. 9 shows reflection and transmission vs. hemoglobin concentration.

FIG. 9 shows light reflection and transmission vs. hemoglobin concentration. When illuminating intact blood. cells in a circular pipe, the light transmission and reflection will follow the concentration of red blood cells. The transmission of light decreases with increased hemoglobin and the reflection of light increases with increased hemoglobin.

EXAMPLE 3

Figure 10:
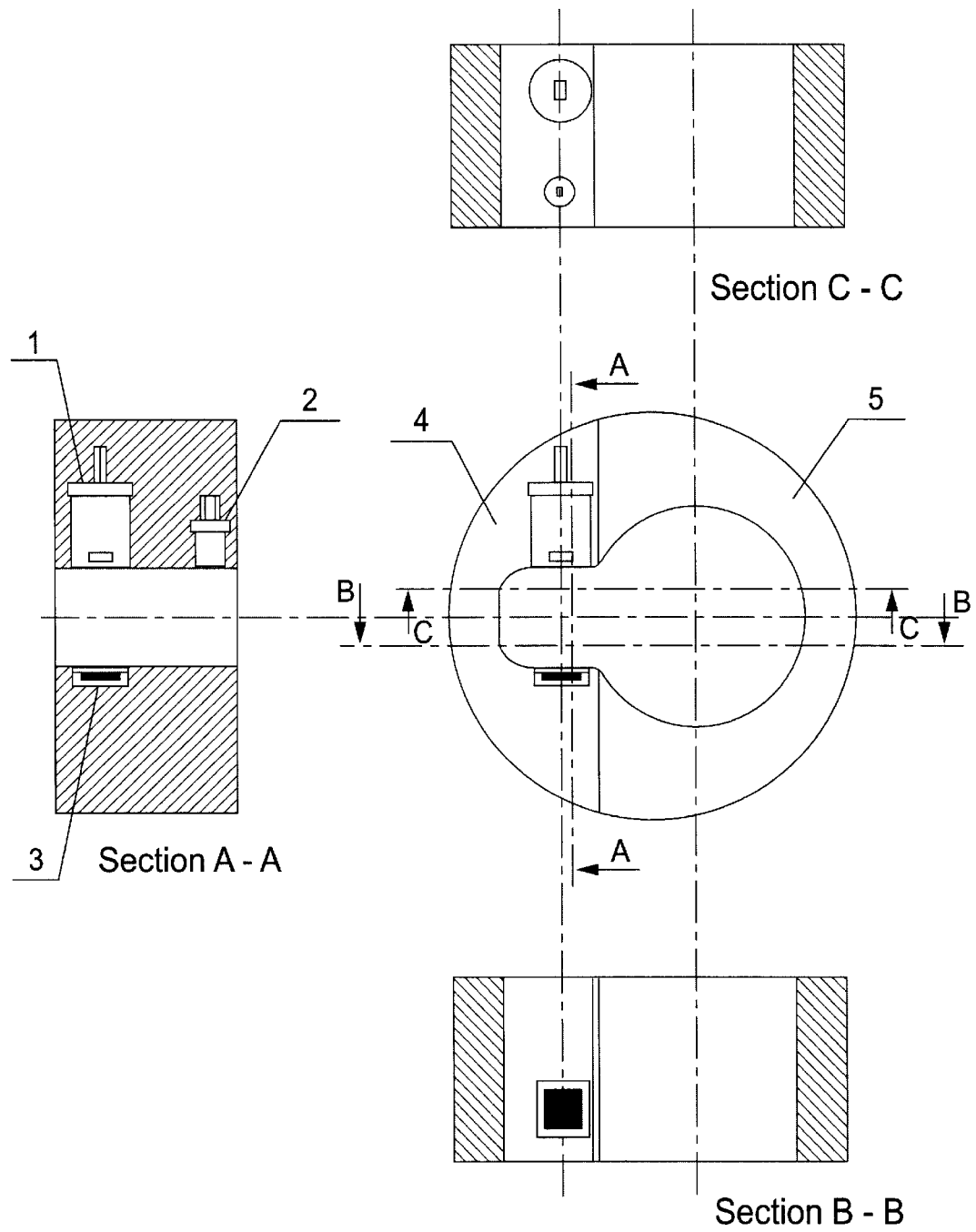
FIG. 10 shows the thimble-like shell construction comprising two light sources, from four different views, without cords.

A thimble-like test device comprising a shell which is one preferred embodiment of the present invention shown in FIG. 10 was used. This thimble comprises:
  i) two light sources: One Green Light Emitting Diode (LED), essentially of type 110104, 540, diameter o 5 mm, and one NIR LED, essentially of type SFH 585, 880, diameter Ø4.85 which are interchangable,
  ii) two detectors, essentially of type SD 1420–002 and CFD 10 respectively.

The thimble has one rigid part comprising a stiffer material and one flexible part comprising a flexible material. The rigid part comprises PMMA or any other similar plastic material. The flexible part comprises silicon rubber with black dye (ceramic pigment which is non-conducting). The rigid and flexible parts form a circular ring forming a keyhole-like hole in the middle, with a bend for e.g. a finger or a toe. The. rigid and flexible parts may be glued together or held together by other means.

How the thimble is connected to a power source and so on, is shown in FIG. 11 through a block diagram illustrating this schematically. The numbers in the figure has the following explanations:
  1. oscillator
  2. LED-Driver $\lambda 1$
  3. LED-Driver $\lambda 2$
  4. LED $\lambda 1$ or 2
  5. Photodiode reflection
  6. Subject
  7. Photodiode transmission
  9. Current/voltage converter
  10. Current/Voltage converter
  11. Lowpass Filter
  12. Lowpass Filter
  13. Sample and Hold amplifier
  14. Sample and Hold amplifier
  15. Band pass Filter
  16. Band pass Filter
  17. Analog output.
  18. Analog output
  19. $\lambda$-controller
  20. Read out unit The oscillator is connected to the Sample and Hold amplifiers and the LED-Driver $\lambda 1$ and LED-Driver $\lambda 2$. These drivers are connected to one or in this case two LEDs and one photodiode for detecting the reflected light. The photodiode for detecting transmitted light is connected to at least one current/voltage converter in this case two, which in turn are connected to the Sample and Hold amplifiers. The signals then pass to the Band pass Filters and subsequently to the analog outputs or to a $\mu$-controller which is connected to a Read out unit.

EXAMPLE 4

A measurement was performed by using an apparatus according to present invention. The relative pressure was monitored and the results can be seen in FIG. 13. The diagram in FIG. 13 shows the intensity of the reflected pulsative light versus increasing systolic pressure. The diastolic pressure was kept constant. This exemplifies the central measurement of blood characteristics including Hb, as represented in larger vessels such as arteries. This is achieved by compensating for the influence of blood pressure and blood flow on the measured intensities of the reflected and transmitted light. The effect may be used to measure the change in blood characteristics including Hb in one individual or in an extracorporeal system when the blood hemoglobin value is constant.

Another measurement was performed by using a probe, where only reflected light was detected, fastened on the wrist (see FIG. 15) of a subject. The probe was placed on the wrist-over the radial artery. Saline was injected in the flow direction close to the probe. The artery needle was inserted 10 cm from the hand into the radial artery with the needle in the flow direction. The distance between the sensor and the tip of the needle was approximately 5 cm. Physiological saline was injected during 1–5 seconds at different volumes. The PPG signal was recorded in order to confirm the monitoring depth. Only the intensity of the reflected light was recorded and the change in signal corresponded to the dilution effect in the blood. The result, i.e. the PPG signal which consists of two components namely a pulsatile component (AC) synchronous with the heart rate and a slowly varying component (DC), can be seen in FIG. 16, where the light reflection showed in change in both AC and DC signals corresponding to dilution effect in the blood after a delay of approximately 0.5 seconds. The DC component reflects total blood volume changes of different physiological features in the circulation, e.g. vasomotion, temperature regulation and respiration.

Various embodiments of the present invention have been described above but a person skilled in the art realizes further minor alterations which would falf into the scope of the present invention. The breadth and scope of the present invention should not be limited by any of the above-described exemplary embodiments, but should be defined only in accordance with the following claims and their equivalents.

What is claimed is:

1. A non-invasive method for the quantitative measurement of haemoglobin concentration in relation to total blood volume in a mixture of liquid and blood cells contained in a light pervious vessel, which comprises
   directing light of at least one wavelength against the vessel;
   detecting the intensity of the light transmitted through the vessel;

detecting the intensity of light reflected from the vessel;

calculating a quotient of said intensity of transmitted light amd reflected light; and analysing said quotient to determine the haemoglobin concentration.

2. The method according to claim 1, wherein the light is directed essentially perpendicular to a measuring area of the vessel, at a wavelength where absorbance on the red blood cells is minimized.

3. A method according to claim 1, wherein the wavelength of the light is from 770 nm to 950 nm.

4. A method according to claim 1, wherein light of two wavelengths is directed against the vessel, one wavelength being in an interval of from 770 nm to 950 nm and the other wavelength being in an interval of from 480 nm to 590 nm.

5. A method according to claim 1, wherein the measurement is performed on a human being.

6. A method according to claim 1, wherein the measurement is performed on a human being and the light pervious vessel is a blood vessel having a diameter >0.1 mm, a vein, an artery or an arteriol.

7. A method according to claim 5, wherein the measurement is performed on a wrist, a toe or a finger.

8. A method according to claim 1, wherein light is emitted from two light sources, which are positioned at opposite sides of the vessel, and wherein the detection of reflected light and transmitted light is performed using two detectors.

9. An apparatus for the quantitative measurement of haemoglobin concentration in relation to total blood volume in a mixture of liquid and blood cells contained in a light pervious vessel, said apparatus comprising at least one light source for directing light of at least one, wavelength against said vessel;

a first detector for detecting the intensity of the light transmitted through said vessel;

a second detector for detecting the intensity of light reflected from said vessel;

processor for calculating a quotient of said intensity of transmitted light and reflected light; and means for analysing said quotient to determine the haemoglobin concentration.

10. An apparatus according to claim 9, wherein said at least one light source is positioned essentially perpendicular to a measuring area of said vessel and capable of emitting light at a wavelength at which the absorbance of red blood cells is minimized.

11. An apparatus according to claim 9, wherein the wavelength of said light is from 770 nm to 950 nm.

12. An apparatus according to claim 9 wherein two light sources are present and light of two wavelengths is directed against said vessel, one wavelength being in the interval of 770 nm to 950 nm, and the other wavelength being in the interval of,480 nm to 590 nm.

13. An apparatus according to claim 9, wherein said first detector is positioned essentially opposite to said light source, and said second detector is positioned alongside said light source.

14. An apparatus according to claim 9, wherein said apparatus further comprises a thimble-like shell suitable for application to a finger or toe of a human being, said light source and detectors arranged to direct the light and to detect transmitted and reflected light within said shell.

15. An apparatus according to claim 9, wherein said apparatus further comprises a handcuff-like shell suitable for application to a wrist of a human being, said light source and arranged to direct the light and to detect transmitted and reflected light within said shell.

16. An apparatus according to claim 9, wherein said apparatus further comprises a flexible part fixing the position of and applying pressure to the vessel.

17. An apparatus according to claim 9, having two light sources arranged on opposite sides of the vessel.

18. A computer program stored on a data carrier, containing instructions for performing the method according to claim 1.

19. An apparatus according to claim 9, said apparatus comprising means for registering and storing the haemoglobin concentration values; and means for visualizing the result of said measurement.

20. A method according to claim 7, wherein the measurement is performed on the third phalanx of a finger.

* * * * *